United States Patent [19]

West

[11] Patent Number: 5,349,087
[45] Date of Patent: Sep. 20, 1994

[54] CARBODIIMIDES AND PROCESSES THEREFOR

[75] Inventor: Michael W. J. West, Wilmington, Del.

[73] Assignee: E. I. Du Pont de Nemours and Company, Wilmington, Del.

[21] Appl. No.: 89,030

[22] Filed: Jul. 13, 1993

Related U.S. Application Data

[62] Division of Ser. No. 875,886, Apr. 29, 1992.

[51] Int. Cl.$^5$ .................... C07C 267/00; C08G 18/16
[52] U.S. Cl. ................................ 564/252; 528/43; 528/51; 528/67
[58] Field of Search ............ 564/252; 528/48, 51, 528/67

[56] References Cited

U.S. PATENT DOCUMENTS

| | | | |
|---|---|---|---|
| 3,406,198 | 10/1968 | Budnick | 260/551 |
| 4,072,712 | 2/1978 | Meisert et al. | 260/566 R |
| 4,137,386 | 1/1979 | Smith | 260/551 CD |
| 4,419,294 | 12/1983 | Feldman et al. | 260/453 A |
| 4,910,339 | 3/1990 | Henning et al. | 564/252 |
| 5,008,363 | 4/1991 | Mallon et al. | 528/49 |
| 5,105,010 | 4/1992 | Sundararaman et al. | 564/252 |

FOREIGN PATENT DOCUMENTS 120305  3/1984  European Pat. Off. ... C07C 119/055

OTHER PUBLICATIONS

K. Wagner et al., *Angew. Chem. Int. ed. Engl.*, 20:819–830 (1981).
K. Kondo et al., *Technol. Rep. Osaka Univ.*, 25:487–489 (1975).
H. Kamogawa et al., *Bull. Chem. Soc. Jap.* 52(2):533–535 (1979).
J. L. Monagle, *J. Org. Chem.* 27:3851–3855 (1962).
T. W. Campbell et al., *J. Org. Chem.* 28:2069–2975 (1963).

*Primary Examiner*—Peter O'Sullivan
*Attorney, Agent, or Firm*—Susan B. Evans

[57] ABSTRACT

Processes are provided for making polycarbodiimides with high carbodiimide contents from isocyanates, and for selectively making mixed aryl-tertiary carbodiimides from isocyanates. Also provided are carbodiimides containing alpha-methylstyryl groups, and polymers made therefrom. All of these polymers and compounds are useful in coatings, and for other applications.

3 Claims, No Drawings

CARBODIIMIDES AND PROCESSES THEREFOR

This is a divisional of Ser. No. 07/875,886, filed on Apr. 29, 1992.

This invention provides selected alpha-methylstyryl substituted carbodiimides and polymers thereof. This invention also provides a process for selectively making tertiary-aryl carbodiimides, and a process for making polymeric carbodiimides with high carbodiimide contents.

Carbodiimides are known in the art, and generalized processes for making them from isocyanates are also known. It is also known in general that these processes are catalyzed by certain compounds, particularly selected phosphorous and arsenic compounds. However, these processes often have drawbacks, such as the inability to control the products obtained when more than one isocyanate is used, and particularly for polymeric carbodiimides, the ability to produce polymers with high carbodiimide contents.

U.S. Pat. No. 4,137,386 discloses the preparation of polystyrene polymers containing dihydrocarbyl arsyl oxide radicals attached to the polymer chain. These polymers are reported to be catalysts for the conversion of organic isocyanates to carbodiimides.

A useful review of polycarbodiimides is K. Wagner, et al., Angew. Chem. Int. Ed. Engl., vol. 20, 819–830 (1981).

SUMMARY OF THE INVENTION

This invention concerns a compound of the formula

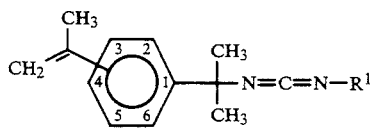

wherein $R^1$ is hydrocarbyl, and provided that the isopropenyl group is in the 3 or 4 position of the benzene ring.

This invention also concerns a polymer, comprising the repeat unit

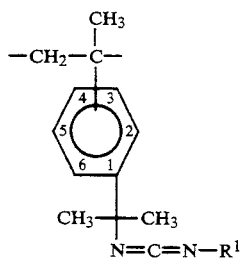

wherein $R^1$ is hydrocarbyl, and provided that the benzene ring is attached to the main polymer chain at the 3 or 4 position of the benzene ring.

The invention also provides a process for the preparation of tertiary-aryl carbodiimides, comprising, contacting a tertiary isocyanate, an aryl isocyanate, and a catalyst for the condensation of isocyanates to carbodiimides, at a sufficiently high temperature and for a sufficient amount of time to convert the isocyanates to carbodiimide, and provided that the selectivity for the tertiary-aryl carbodiimide is greater than it is for random reaction.

This invention also concerns a process for making polymeric carbodiimides, comprising, contacting one or more diisocyanates with a triarylarsine oxide, at a sufficiently high temperature and for a sufficient amount of time to react of 90% or more of the original isocyanate groups, and provided that the total of primary and secondary isocyanate groups present is at least 10% of the total isocyanate groups present.

DETAILS OF THE INVENTION

In the compound of the formula

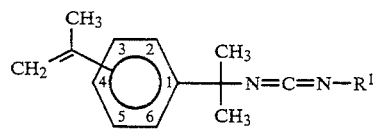

$R^1$ is hydrocarbyl. By hydrocarbyl herein is meant a monovalent radical containing only carbon and hydrogen. It is preferred if $R^1$ (in both the monomeric compound and polymer herein) contains 1–25 carbon atoms and more preferred if $R^1$ is alkyl containing 1 to 6 carbon atoms, cyclohexyl, or aryl. It is most preferred if $R^1$ is phenyl, isopropyl and cyclohexyl. These monomeric carbodiimides can be made by known methods, such as the phospholene oxide or triarylarsine oxide catalyzed condensation of the corresponding isocyanates (see Examples 1–6, herein), or dehydration of the corresponding ureas (see for example K. Kondo, et al., Technol. Rep. Osaka Univ., vol. 25, 487–489 (1975) or H. Kamagawa et al., Bul. Chem. Soc. Japan., vol. 52, 533–535 (1979). The monomeric carbodiimides containing alpha-methylstyryl groups are useful as monomers for the preparation of polymers (see below).

These alpha-methylstyryl group containing carbodiimides may be polymerized by free radical polymerization to form polymers with the repeat unit shown above. They may be homopolymerized or copolymerized, so the term "comprising" for these polymers includes both homopolymers and copolymers. Copolymerization may be carried out with comonomers that normally copolymerize with alpha-methylstyrene, and these comonomers are known in the art. Preferred comonomers are styrene, maleic anhydride, itaconic anhydride, and acrylic (including methacrylic) esters. The polymerizations are carried out according to known procedures.

Polymers containing units derived from the alphamethylstyryl group containing carbodiimide are reactive with compounds and groups containing active hydrogen atoms, such as water, hydroxyl (alcohols), carboxyl, phosphoric acid and partial esters thereof, and primary and secondary amino. Therefore they are useful as polymeric dehydrating agents, or can be used to crosslink other polymers which contain the above mentioned functional groups, particularly carboxyl and primary and secondary amino. This ability to crosslink polymers containing active hydrogen makes these carbodiimide polymers useful in coatings, where it is common to form a crosslinked coating by mixing two mutually reactive polymers which crosslink each other to form the final polymer coating. They are particularly useful in coatings for automobiles. They are also useful in wood finishes, and as ingredients in printing inks, photoresists, and for polymer film coatings such as photographic film coatings and coatings for fibers.

Also disclosed herein is a process for the production of tertiary-aryl carbodiimides from tertiary and aryl isocyanates. Throughout this Application, the following terms are used:

primary isocyanate or carbodiimide—An isocyanate in which the nitrogen atom is bound to a primary alkyl carbon atom (a carbon atom bound to only one other carbon atom), or a carbodiimide in which one of the nitrogen atoms of the carbodiimide group is bound to a primary carbon atom.

secondary isocyanate or carbodiimide—An isocyanate in which the nitrogen atom is bound so a secondary (cyclo)alkyl carbon atom (a carbon atom bound to only two other carbon atoms), or a carbodiimide in which one of the nitrogen atoms of the carbodiimide group is bound to a secondary (cyclo)carbon atom.

tertiary isocyanate or carbodiimide—An isocyanate in which the nitrogen atom is bound to a tertiary (cyclo)alkyl carbon atom (a carbon atom bound to three other carbon atoms), or a carbodiimide in which one of the nitrogen atoms of the carbodiimide group is bound to a tertiary (cyclo)alkyl carbon atom.

aryl isocyanate or carbodiimide—An isocyanate in which the nitrogen atom is bound to a carbon atom of an aromatic ring, or a carbodiimide in which one of the nitrogen atoms of the carbodiimide group is bound to a carbon atom of an aromatic ring.

Since a carbodiimide group has two nitrogen atoms, the complete molecule will require a designation of the groups on both of the nitrogen atoms, such as a tertiary-aryl carbodiimide, a ditertiary carbodiimide, etc.

Carbodiimides can be made by the condensation of isocyanate groups, and this is usually done in the presence of a catalyst. When two different isocyanates, $R^2NCO$ and $R^3NCO$, of equal reactivity are used in equimolar amounts, one expects a mixture of carbodiimides, $R^2NCNR^2$, $R^2NCNR^3$ and $R^3NCNR^3$, in the molar ratio 1:2:1 respectively. If the reactivities of one of the isocyanates is greater than the other, one expects larger and larger amounts of $R^2NCNR^2$ and $R^3NCNR^3$, and lesser amounts of the "mixed" carbodiimide $R^2NCNR^3$. The amount of mixed carbodiimide would be expected to decrease as the difference in the relative reactivities increases. Thus the maximum amount of mixed carbodiimide normally expected would be about 50 mole percent. For this reason, the art skilled have developed alternate syntheses of mixed carbodiimides, such as using ureas as intermediates (see for example H. Kamogawa, et al., supra).

It has suprisingly been found that when an aryl isocyanate is mixed with a tertiary isocyanate in the presence of a catalyst for the condensation to carbodiimide, much higher than expected amounts of the aryl-tertiary carbodiimide are formed, and in some cases the product is relatively pure aryl-tertiary carbodiimide. It has also been found that when diisocyanates are used in this process that unique polymers may result. For example if a bis(aryl isocyanate) is reacted with a bis(tertiary isocyanate), the product will be predominantly an alternating carbodiimide copolymer, with the alternating units being derived from the two isocyanates. More exactly, one obtains an alternating polycarbodiimide in which one of the alternating units is directly connected to two adjacent carbodiimide groups through aromatic carbon atoms, and the other alternating unit is directly connected to two adjacent carbodiimide units through tertiary alkyl carbon atoms. It is preferred if at least 80% of the units in the polymer are alternating. Similarly, if a diisocyanate containing one aryl isocyanate and one tertiary isocyanate is used, the resulting polymer will be one in which the monomeric units are attached to one another in a predominantly head to tail fashion.

This process is carried out in the presence of catalyst for the condensation of isocyanates to carbodiimides, and these are known in the art (see for example K. Wagner, et al., supra). Preferred catalysts in the process are phospholene oxides and triarylarsine oxides. The process is carried out at a sufficient temperature and for a sufficient amount of time so that the condensation to carbodiimide is accomplished. This will vary according to the isocyanates and catalyst used, and can be easily determined for any set of reactants. A convenient temperature range is about 0° C. to about 250° C., preferably about 120° C. to about 160° C. The progress of the reaction can be monitored by a variety of techniques, for example infrared spectroscopy. In order to avoid decomposing either the starting materials or products the reaction should be carried out in the absence compounds containing active hydrogen, such as water. This is conveniently done by carrying out the process under an inert gas such as nitrogen. Although inert solvents may be used, it is preferred if the process is carried out without solvent when monomeric compounds are being made.

Aryl isocyanates useful in this process include, but are not limited to, phenyl isocyanate, bis(4-isocyanatophenyl)methane, diisocyanatobenzene, and 2,4-toluenediisocyanate. 2,4-Toluenediisocyanate is a preferred aromatic isocyanate. Useful tertiary isocyanates include, but are not limited to, t-butylisocyanate, 1,4-bis(2-isocyanato-2-propyl)benzene, 2-(3-isopropenylphenyl)-2-isocyanatopropane, 2-(4-isopropenylphenyl)-2-isocyanatopropane, and 1,3-bis(2-isocyanato-2-propyl)benzene. A preferred polymer product is one obtained from 1,3- or 1,4-bis(2-isocyanato-2-propyl)benzene and bis (4-isocyanatophenyl)methane.

The aryl-tertiary mono- and polycarbodimides are useful as drying and dehydrating agents. In addition, reaction of these compounds with one mole of carboxylic acid per equivalent of carbodiimide leads to a N-aryl-N-acyl-N'-tertiaryalkylurea, which upon thermolysis yields an N-arylamide and a tertiary isocyanate [see Y. Iwakura, et al., Polym. Lett., vol. 6 p. 517–522 (1968)]. These aryl-tertiary carbodiimides, after reaction with carboxylic acid, give compounds which are masked alkyl isocyanates. Alkyl isocyanates (and their reaction products) are particularly useful in coatings, where they are very resistant to color change. When a polycarbodiimide is used to make the N-aryl-N-acyl-N'-tertiaryalkylurea, the product after thermolysis is a bis(tertiaryisocyanate) which can be used to crosslink polymers with functional groups that react with isocyanates. The advantage of using the N-aryl-N-acyl-N'-tertiaryalkylurea instead of the bis(tertiaryisocyanate) directly is that the urea is generally much less toxic than the diisocyanate.

Also described herein is a process for making polycarbodiimides which are suitable for use in coatings. Polycarbodiimides are useful in coatings because carbodiimide groups react with many functional groups such as carboxylic acid, alcohols and primary and secondary amines, and can crosslink polymers which contain these functional groups. Crosslinking of such polymers is often the curing step for coatings. Carbodiimides are toxic, so it is preferable if the carbodiimides are in polymeric form to reduce their vapor pressure (these coatings are often applied as sprays).

In the instant process, a triarylarsine oxide is used as the catalyst. Useful triarylarsine oxides include, but are not limited to, triphenylarsine oxide, tri-p-tolylarsine oxide, trinaphthylarsine oxide, tris[(4-phenyl)phenyl]arsine oxide, and polymer bound arsine oxides. Triphenylarsine oxide is a preferred catalyst. Although not critical, the amount of catalyst used can range from about 0.0001% to about 3% by weight of the isocyanate compounds initially present, preferably about 0.01% to about 0.5% by weight of the isocyanate compounds initially present.

The isocyanates used in the process will generally be diisocyanates. Small amounts of monoisocyanates may be present to act as an endcapping agent. Endcapping agents are used to provide nonisocyanate ends to the polycarbodiimides, see for example T. W. Campbell, et. al., J. Org. Chem., vol. 28, p. 2069–2075 (1963), for a discussion of endcapping of polycarbodiimides. Any diisocyanates may be used in the process. Useful diisocyanates include, but are not limited to, bis(4-isocyanatophenyl)methane, 2,4-toluenediisocyanate 1,4-bis(2-isocyanato-2-propyl)benzene, 1,3-bis(2-isocyanato-2-propyl)benzene, 1,2-, 1,3- and 1,4-diisocyanatocyclohexane, 1,6-hexanedioscyanante, isophorone diisocyanate, trimethyl-1,6-hexanediisocyanate, and bis(4-isocyanatocyclohexyl)methane.

The process is carried out at a temperature of 0° C. to 300° C., preferably about 20° C. to about 200° C., and more preferably about 100° C. to about 160° C. Although not necessary, the process may be carried out in the presence of an inert solvent. Examples of suitable solvents are propylene glycol methyl ether acetate, xylene, toluene, propyl acetate, butyl ether, chlorobenzene, o-dichlorobenzene, and dichloroethylene. It is preferred if a solvent is present. Solvents containing active hydrogen atoms (e.g., alcohols) should not be used. It is preferred that the final product is soluble in solvents, i.e., has not gelled, since soluble polycarbodiimides are preferred for use in coatings. Process times will vary according to the isocyanates used, the product desired, the type and amount of catalyst used, the temperature, etc. Generally process times will range from 0.1 to 24 hr., typically 1 to 10 hr. The reaction may be followed by a variety of techniques, for example infrared spectroscopy.

Compounds containing active hydrogen, such as water vapor, are deleterious, so it is convenient to carry out the process under an inert gas such as nitrogen or dry air.

In the instant process at least 10% of the total initial isocyanate groups are primary and/or secondary isocyanates, that is the total of the primary and secondary isocyanates are at least about 10% of the initial isocyanate groups. It is preferred if 25% of the initial isocyanates groups are primary and/or secondary isocyanates, and more preferred if at least about 50% of the initial isocyanates groups are primary and/or secondary isocyanate groups.

In the instant process it has been found that the resulting polycarbodiimide has a relatively high carbodiimide content. It is preferred if 90% or more of the original isocyanate groups are reacted, more preferably 95% or more. By original isocyanate groups are meant all of the isocyanate groups initially present minus those groups that are reacted with alcohols, etc. to endcap the polymers. Assuming complete conversion of the original isocyanate groups to carbodiimide groups, for every two starting isocyanate groups, one should obtain one carbodiimide group. The reacted isocyanate groups include all isocyanate groups that could have formed carbodiimides, but does not include for example, isocyanate groups that are used to endcap the polymer where the endcapping reaction does not form a carbodiimide, such as reaction with an alcohol. It is known in these types of polymerizations that side reactions reduce the actual number of carbodiimide groups in the polycarbodiimide below that theoretically attainable. In the instant process it is preferred if 70% or more of the theoretical number of carbodiimide groups are obtained, and more preferably 90% or more. In general, it is preferred to obtain a polycarbodiimide with as high (compared to the theoretical amount) a carbodiimide content as possible.

One of the important parameters herein is the carbodiimide content of a polycarbodiimide. This is measured by the procedure described by W. Adam and F. Yany, Analytical Chemistry, vol. 49 p. 676 (1977) which is slightly modified. Usually tetrahydrofuran solutions of the reactants are used, and the times of reaction are varied from 1 to 48 hr., the longer times being used for hindered, somewhat insoluble, or aromatic carbodiimides.

Reactions were typically carried out in 500 mL 3-necked round bottom flasks equipped with nitrogen inlet, bubbler outlet (equipped with an apparatus to measure gas evolved), water-cooled reflux condenser, mechanical or magnetic stirrer, thermocouples for temperature measurement, septum capped inlet for addition of materials, and heated by a heating mantle (sometimes controlled with a temperature controller) or similar apparatus.

EXAMPLE 1

1-Phenyl-3-[2-(3-isopropenylphenyl)-2-propyl]carbodiimide

We combined 0.3182 g 3-methyl-1-phenyl-2-phospholene-1-oxide (MPPO), m-TMI [2-(3-isopropenylphenyl)-2-propylisocyanate], and 19.31 g phenyl isocyanate. After heating at 140°–150° C. for 14 hours, IR showed nearly complete conversion of isocyanates to carbodiimides. GC-MS integrated ionization current shows a response of 265944 units for the title mixed product, 3558 units for the diphenyl carbodiimide, and 3602 units for the ditertiarycarbodiimide. Assuming that the detector sensitivity for the mixed product is the same, the selectivity for the mixed product is the average of the two other products, the reaction selectivity for the mixed product is 265944/(265944+3602+3558) or 97%, so the maximum yield of either mixed product is 3%.

EXAMPLE 2

1-Phenyl-3-[2-(3-isopropenylphenyl)-2-propyl]carbodiimide

We combined 0.0982 g TPAO, 19.30 g benzyl acetate (internal standard), 60.40 g of m-TMI, and 35.77 g phenyl isocyanate. Heating at 150° C. was carried out for 6 hours; at 2 hours IR showed nearly complete conversion of isocyanates to carbodiimides. GC-FID showed that product was predominantly the title carbodiimide (89.3%), unreacted TMI (4.2%) and 1,3-bis[2-(3-isopropenylphenyl-2-propyl]carbodiimide (4.2%) and 1,3-diphenylcarbodiimide (2.9%) versus internal standard. Material from this Example was distilled to obtain in 71% recovery on products of a purified sample (92% pure) of the title product and in 6% recovery on products of a crude (66% purity) sample of the same product.

EXAMPLE 3

1-Isopropyl-3-[2-(3-isopropenylphenyl)-2-propyl]carbodiimide

We combined 0.0820 g TPAO, 60.46 g of m-TMI, and 12.63 g 1,3-diisopropylcarbodiimide. After heating at 150° C. for 5 hours, a further 0.0857 g TPAO was added. Heating was continued 4 further hours. IR showed complete conversion of isocyanates to carbodiimides. The mixed carbodiimide forms about 51% molar of the product, as determined by $^1$H-NMR.

EXAMPLE 4

1-Isopropyl-3-[2-(3-isopropenylphenyl)-2-propyl]carbodiimide

We combined 0.1145 g TPAO, 60.45 g of m-TMI, and 28.42 g 1,3-diisopropylcarbodiimide. After heating at 150° C. for 2 hours, a further 0.1047 g triphenylarsine oxide (TPAO) was added. Heating was continued 3 further hours. A further 0.1084 g triphenylarsine oxide (TPAO) was added. Heating was continued 6 further hours. IR showed nearly complete conversion of isocyanates to carbodiimides. Material was distilled to obtain in 50% recovery a purified sample of the title product, as verified by $^1$H-NMR.

EXAMPLE 5

1-Cyclohexyl-3-[2-(3-isopropenylphenyl)-2-propyl]carbodiimide

We combined 0.0804 g TPAO, 60.43 g of m-TMI, and 20.61 g 1,3-dicyclohexylcarbodiimide. After heating at 150° C. for 6 hours, IR showed nearly complete conversion of isocyanates to carbodiimides. $1_H$-NMR indicated the desired product contaminated with 1,3-dicyclohexylcarbodiimide, and 1,3-bis[2-(3-isopropenylphenyl)-2-propyl]carbodiimide.

Distillation provided a fraction (11% by weight) of mostly dicyclohexylcarbodiimide, and another fraction (37% by weight) of mostly the other homocarbodiimide, and other fractions which contained all three products. The title product constitutes less than 52% by weight of the product mixture.

EXAMPLE 6

1-Cyclohexyl-3-[2-(3-isopropenylphenyl)-2-propyl]carbodiimide

We combined 0.0830 g TPAO, 60.41 g of m-TMI, and 25.04 g cyclohexylisocyanate. After heating at 150° C. for 7 hours, IR showed nearly complete conversion of isocyanates to carbodiimides. $^1$H-NMR indicated the desired product contaminated with 1,3-dicyclohexylcarbodiimide, and 1,3-bis[2-(3-isopropenylphenyl)-2-propyl]carbodiimide.

EXAMPLE 7

Under nitrogen were combined 109.67 g methyl ether polyethylene oxide (average molecular weight 750 g/mole), 357.43 g isophorone diisocyanate, 400.42 g propylene glycol methyl ether acetate, and 0.8246 g 2-ethylhexylglycidyl ether. The mixture was refluxed for 2 hours, cooled, and 0.7159 g triphenylarsine oxide hydrate was added. The mixture was refluxed 2 hours, at which time IR demonstrated no peak around 2200 cm$^{-1}$, and a strong peak around 2100 cm$^{-1}$. A solids determination showed 50.7% solids; a carbodiimide titration showed 1.75 mM/g solution. (Theory, 50%, 1.92 mM/g-solution.)

EXAMPLE 8

Under nitrogen were combined 26.5329 g isophorone diisocyanate, 1.5260 g cyclohexyl isocyanate, 22.5389 g xylenes, and 0.0077 g triphenylarsine oxide hydrate. The mixture was refluxed 3 hours, at which time IR demonstrated no peak around 2100 cm$^{-1}$, and a strong peak around 2200 cm$^{-1}$. A further 0.0327 g triphenylarsine oxide hydrate was added. Reflux was continued another hour, then the reaction mixture was held at room temperature overnight. Reflux was continued 2 further hours, at which time IR demonstrated no peak around 2200 cm$^{-1}$, and a strong peak around 2100 cm$^{-1}$.

A solids determination showed 69.9% solids (loss during reflux?); a carbodiimide titration showed 3.45 mM/g solution. (Theory, 50%, 2.78 mM/g-solution; expect 3.89 at 69.9% solids.)

EXAMPLE 9

Under nitrogen were combined 35.21 g methyl ether polyethylene oxide (average molecular weight 750 g/mole), 135.76 g bis(4-isocyanatocyclohexyl)-methane, 150.12 g propylene glycol methyl ether acetate. The mixture was refluxed for 1 hour, cooled, and 0.1533 g triphenylarsine oxide hydrate was added. The mixture was refluxed 3 hours, at which time IR demonstrated a very small peak around 2200 cm$^{-1}$, and a strong peak around 2100 cm$^{-1}$. A solids determination showed 50.5% solids; a carbodiimide titration showed 1.65 mM/g solution. (Theory, 50%, 1.72 mM/g-solution.)

EXAMPLE 10

A 500 mL 3-neck round bottom flask with nitrogen flush, mechanical stirrer, reflux condenser, was charged with 0.2168 g triphenylarsine oxide, 71.23 g methylene bis(4-isocyanatocyclohexane), 0.87 g cyclohexylisocyanate, (expected degree of polymerization=78) and 240.07 g xylene. The mixture was heated at reflux for 3 hour, at which time IR showed no peak around 2200 cm$^{-1}$ for NCO, and a large peak around 2100 cm$^{-1}$ for NCN. The product was soluble in THF, but phase-separated from propylene glycol methyl ether acetate. The product was 20.9% solids, and had a carbodiimide content of 0.89 mM/g. (Theory, 0.95 mM/g.)

EXAMPLE 11

Under nitrogen were combined 57.45 g methyl ether polyethylene oxide (average molecular weight 750 g/mole), 60.29 g bis(4-isocyanatocyclohexyl)methane, 50.93 g isophorone diisocyanate, 57.45 g propylene glycol methyl ether acetate. The mixture was refluxed for 2 hours, cooled, and 0.2485 g triphenylarsine oxide hydrate was added. The mixture was refluxed 3 hours, at which time IR demonstrated no peak around 2200 cm$^{-1}$, and a strong peak around 2100 cm$^{-1}$. A solids determination showed 50.5% solids; a carbodiimide titration showed 1.34 mM/g solution. (Theory, 50%, 1.40 mM/g-solution.)

EXAMPLE 12

Under nitrogen were combined 46.35 g methyl ether polyethylene oxide (average molecular weight 750 g/mole), 41.48 g tetramethyl-meta-xylylene diisocyanate, 37.82 g isophorone diisocyanate, 125.52 g propylene glycol methyl ether acetate. The mixture was heated to 100° C. for 1.5 hours, cooled, and 0.1789 g triphenylarsine oxide hydrate and 15.50 g cyclohexyl isocyanate were added. The mixture was refluxed 4 hours, at which time IR demonstrated a very small peak around 2200 cm$^{-1}$, and a strong peak around 2100 cm$^{-1}$. A solids determination showed 50.0% solids; a carbodiimide titration showed 1.41 mM/g solution. (Theory, 49.8%, 1.48 mM/g-solution.)

EXAMPLE 13

Under nitrogen were combined 17.24 g tetramethyl-meta-xylylene diisocyanate, 7.92 g 1,6-diisocyanatohexane, 2.98 g cyclohexyl isocyanate, 25.02 g xylenes, and 0.0194 g triphenylarsine oxide hydrate. The mixture was refluxed 5 hours, and a further 0.0307 g triphenylarsine oxide hydrate was added. Reflux was continued a further 3 hours, held at room temperature over a weekend, and continued a further 5 hours, at which time IR demonstrated no peak around 2200 cm$^{-1}$, and a strong peak around 2100 cm$^{-1}$. A solids determination showed 54.5% solids; a carbodiimide titration showed 2.64 mM/g solution. (Theory, 47.3%, 3.14 mM/g-solution at 54.5% solids due to solvent loss.)

EXAMPLE 14

Under nitrogen were combined 115.12 g bis(4-isocyanatocyclohexyl)methane, 24.59 g 1,6-diisocyanatohexane, 0.9232 g 2-ethylhexylglycidyl ether, and 125.28 g propylene glycol methyl ether acetate. The mixture was refluxed for 2 hours, cooled, and there was added 12.17 g cyclohexyl isocyanate, and 0.1581 g triphenylarsine oxide hydrate. The mixture was refluxed 4 hours, and a further 0.0346 g triphenylarsine oxide hydrate was added. Reflux was continued a further 2 hours, at which time IR demonstrated no peak around 2200 cm$^{-1}$, and a strong peak around 2100 cm$^{-1}$. A solids determination showed 49.3% solids; a carbodiimide titration showed 2.29 mM/g solution. (Theory, 49.9%, 2.52 mM/g-solution.)

EXAMPLE 15

In a 500 mL flask with nitrogen flushing, were placed 0.0883 g triphenylarsine oxide, 58.98 g isophorone diisocyanate, 31.51 g phenyl isocyanate, 23.03 g toluene diisocyanate, and 110.02 g xylenes. After 2 hours reflux, no IR absorbance could be detected around 2200 cm$^{-1}$ for isocyanate. Solids was 45.6%. The back titration with oxalic acid, after 24 hours reaction, showed a carbodiimide content of 2.13 mM/g, 80% of theory.

COMPARATIVE EXPERIMENT 1

In a 500 mL flask with nitrogen flushing, were placed 0.5294 g 3-methyl-1-phenyl-phospholene-1-oxide, 59.18 g isophorone diisocyanate, 31.38 g phenyl isocyanate, 22.94 g toluene diisocyanate, and 110.07 g xylenes. After 2 hours reflux, some IR absorbance could be detected around 2200 cm$^{-1}$ for isocyanate. After 6 hours reflux, no peak could be detected. Solids was 47.6%. The back titration with oxalic acid, after 24 hours reaction, showed a carbodiimide content of 1.62 mM/g, 61% of theory.

EXAMPLE 16

A mixture of bis(4,4'-diisocyanatophenyl)methane (80.47 g), alpha,alpha,alpha',alpha'-tetramethyl-1,3-xylylene diisocyanate (94.34 g), phenyl isocyanate (7.66 g), xylene (150 g) and triphenylarsine oxide (0.2153 g) were combined under nitrogen flushing and refluxed for 5 hours. Titration demonstrated a carbodiimide content of 2.46 mM/g, and solids were 52.1 wt %. $^1$NMR analysis demonstrated that 85–95% of the maximum amount of mixed unsymmetrical carbodiimide (alternating copolymer) had been formed.

$^1$H-NMR resonance positions were established through comparison of spectra of a (1) polymer of alpha,alpha, alpha',alpha'-tetramethyl-1,3-xylylene-carbodiimide, (2) biscarbodiimide of alpha,alpha,alpha',alpha'-tetramethyl-1,3-xylylenediisocyanate and 2 moles of phenyl isocyanate, and the (3) monomer 1-phenyl[2-(3-isopropenylphenyl)-2-propyl]carbodiimide with the product. For (1), H(2) (the hydrogen on aromatic carbon 2 of the xylylene nucleus) was at delta=7.735 PPM, while the methyl group was at 1.766. For (2), H(2) was at 7.651, and the methyl at 1.723; for (3), the H(2) was at 7.623, and the methyl was at 1.607. From this, we conclude that the copolymer where two alpha,alpha,alpha',alpha'-tetramethyl-1,3-xylyl groups are joined as a carbodiimide should have 4 methyl groups resonating around 1.601 PPM; whereas a mixed carbodiimide would show methyl groups at around 1.7+; similarly, the H(2) should appear around 7.623 (aliphatic) and 7.70+/−0.05 (mixed) respectively. The product showed resonances at 1.601 (relative area 2.1) and a complex pattern of 1 greatly predominant peak at 1.715 (relative area 18). Similar results were seen in the aromatic region for H(2); a major complex at around 7.725 (area 1.4), and a minor complex at around 7.667 (area 0.3); however, experimental error was much higher.

EXAMPLE 17

In a 250 mL 3-neck flask with nitrogen flushing, magnetic stirring, reflux condenser, were combined 42.35 g propylene glycol methyl ether acetate, 45.01 g isophorone diisocyanate, 4.52 g of polyethylene oxide methyl ether (MW=750), 1.50 g n-butyl isocyanate, and 0.0826 g triphenylarsine oxide. After 2 hours reflux at about 152° C., IR showed no isocyanate absorbance, and a very strong absorbance due to carbodiimide. After storage for about 300 days, Gardner-Holt Viscosity was R, and carbodiimide content was 2.2 mM/(gram solution), versus a theoretical yield of 2.4 mM/(gram solution), without correction for any loss of volatiles.

COMPARATIVE EXAMPLE 2

In a 250 mL 3-neck flask with nitrogen flushing, magnetic stirring, reflux condenser, were combined 38.28 g propylene glycol methyl ether acetate, 45.44 g isophorone diisocyanate, 4.56 g of polyethylene oxide methyl ether (MW=750), 1.51 g n-butyl isocyanate, and 4.70 g of 10% 3-methyl-1-phenyl-2-pholene-1-oxide in xylene. After 4 hours reflux at about 152° C., IR showed a substantial isocyanate absorbance, about 25% of the size of the strong absorbance due to carbodiimide. At 7 hours reflux, this peak was still easily recognized, as about 4% of the strong carbodiimide peak. After 11 hours of reflux, the reaction mixture gelled.

EXAMPLE 18

In a 100 mL flask with nitrogen flush, mechanical stirrer, reflux condenser, were placed 0.0859 g triphenylarsine oxide, 33.4560 g isophorone diisocyanate, 1.4919 g n-butyl isocyanate, and 25.0234 g propylene glycol methyl ether acetate. The mixture was refluxed at about 145° C. for 1 hour, when IR showed the isocyanate peak to be about 4% of the carbodiimide peak. Soon after, the solution was cooled, and 8 days later was noted to be an easily-flowing liquid.

COMPARATIVE EXAMPLE 3

In a 100 mL flask with nitrogen flush, mechanical stirrer, reflux condenser, were placed 33.5565 g isophorone diisocyanate, 1.4616 g n-butyl isocyanate, 25.5440 g propylene glycol methyl ether acetate, and 8.0 g of 10% 3-methyl-1-phenyl-2-phospholene-1-oxide in xylene. The mixture was refluxed at about 145° C. for 8 hours, at which time a significant concentration of isocyanate could be detected by IR. When the viscous liquid was allowed to cool, it gelled.

EXAMPLE 19

A 1 liter flask was sparged with nitrogen at 40 mL/min. Isophorone diisocyanate (181.51 g), xylenes (14.34 g) and triphenylarsine oxide (0.1442 g) were charged. The contents were heated to ca. 145° C., at which time gas evolution of up to 760 mL/min was noted, as measured by a Sierra Instruments Top-Trak mass flowmeter calibrated to air. After less than 50 minutes, the flask contents were cooled to less than 60° C., effectively stopping gas generation after evolution of ca. 12 liters of gas. n-Butanol (15.71 g), methyl ether of polyethylene oxide (MW=750 nominal) (116.54 g), and propylene glycol methyl ether acetate (234.75 g) were added; separately toluene diisocyanate (56.96 g) and further propylene glycol methyl ehter acetate (130.0 g) were also added. The contents were heated to ca. 110° C. for 1 hour, then raised to ca. 146°-150° C. for 3.5 hours. IR showed complete conversion of isocyanate groups. Gardner-Holt bubble tube viscosity was A to A-1, solids was 47.1%, and carbodiimide content by oxalic acid back titration was 0.82+/−0.02 mM/g. Theoretical yield is 1.356 mM/g.

COMPARATIVE EXAMPLE 4

A 1 liter flask was sparged with nitrogen at 40 mL/min. Isophorone diisocyanate (181.55 g), and a solution of 10 wt % MPPO in xylenes (14.31 g) were charged. The contents were heated to ca. 145° C., at which time gas evolution of up to 180 mL/min was noted, as measured by a Sierra Instruments Top-Trak mass flowmeter calibrated to air. After about 2 hours, the flask contents were cooled, effectively stopping gas generation after evolution of ca. 12.4 liters of gas. n-Butanol (15.71 g), methyl ether of polyethylene oxide (MW=750 nominal) (116.53 g), and propylene glycol methyl ether acetate (234.02 g) were added; separately toluene diisocyanate (56.91 g) and further propylene glycol methyl ether acetate (130.0 g) were also added. The contents were heated to ca. 110° C. for 1 hour, then raised to ca. 146°-150° C. for 11 hours. IR showed almost complete conversion of isocyanate groups. Gardner-Holt bubble tube viscosity was A-1, solids was 47.2%, and carbodiimide content by oxalic acid back titration was 0.63 mM/g. Theoretical yield is 1.358 mM/g.

What is claimed is:

1. An alternating polycarbodiimide in which a first alternating unit is directly connected to two adjacent carbodiimide groups through aromatic carbon atoms, and a second alternating unit is directly connected to two adjacent carbodiimide units through tertiary alkyl carbon atoms.

2. The polymer as recited in claim 1 wherein at least 80% of the units are alternating.

3. The polymer as recited in claim 1 wherein said first alternating unit is

—⟨C₆H₄⟩—CH₂—⟨C₆H₄⟩—N=C=N— and said second alternating unit is

—C(CH₃)₂—⟨C₆H₄⟩—C(CH₃)₂—N=C=N— wherein said second alternating unit is 1,3 or 1,4 ring substituted.

* * * * *